(12) United States Patent
Carmichael et al.

(10) Patent No.: US 9,782,182 B2
(45) Date of Patent: Oct. 10, 2017

(54) ABDOMINAL AORTIC TOURNIQUET

(71) Applicant: TREBOR INDUSTRIES, INC., Pompano Beach, FL (US)

(72) Inventors: Robert Manuel Carmichael, Pompano Beach, FL (US); Jeff Morris, Pompano Beach, FL (US); Stephen Grasso, Pompano Beach, FL (US)

(73) Assignee: TREBOR INDUSTRIES, INC., Pompano Beach, FL (US)

( * ) Notice: Subject to any disclaimer, the term of this patent is extended or adjusted under 35 U.S.C. 154(b) by 0 days.

(21) Appl. No.: 15/168,391

(22) Filed: May 31, 2016

(65) Prior Publication Data
US 2016/0345980 A1 Dec. 1, 2016

Related U.S. Application Data

(63) Continuation of application No. 14/064,134, filed on Oct. 26, 2013, now Pat. No. 9,351,737.

(60) Provisional application No. 61/719,194, filed on Oct. 26, 2012.

(51) Int. Cl.
*A61B 17/135* (2006.01)
*A61B 17/132* (2006.01)

(52) U.S. Cl.
CPC ........ *A61B 17/135* (2013.01); *A61B 17/1322* (2013.01)

(58) Field of Classification Search
CPC ... A61B 17/1325; A61B 17/135; A61B 5/022; A61B 5/02233; A61H 9/0078; A61F 5/05816
USPC ....... 606/201–204, 204.15, 204.35; 600/490, 600/499; 601/151, 152; 602/13, 41, 53, 602/60–66, 75; 128/869, 870, 96.1
See application file for complete search history.

(56) References Cited

U.S. PATENT DOCUMENTS

2013/0310872 A1* 11/2013 Croushorn ......... A61B 17/1325
606/202

* cited by examiner

*Primary Examiner* — Eric Rosen
*Assistant Examiner* — George J Ulsh
(74) *Attorney, Agent, or Firm* — Daniel S. Polley, P.A.

(57) ABSTRACT

An abdominal aortic tourniquet having one-piece member for the bladder and cover portions and whose bladder has a triangular cross-sectional shape when inflated that significantly increases the amount of point pressure such that the intended artery is properly occluded. The one-piece bladder/cover design provides for a reduction in cost of materials and provides for a more compact piece as compared to prior designs. The abdominal aortic tourniquet uses a single piece of weldable and gas impermeable fabric that is configured in a novel manner to create a three-dimensional, pneumatic piston while also serving as storage/transport cover, attachment structure, and major component of the belt member.

21 Claims, 9 Drawing Sheets

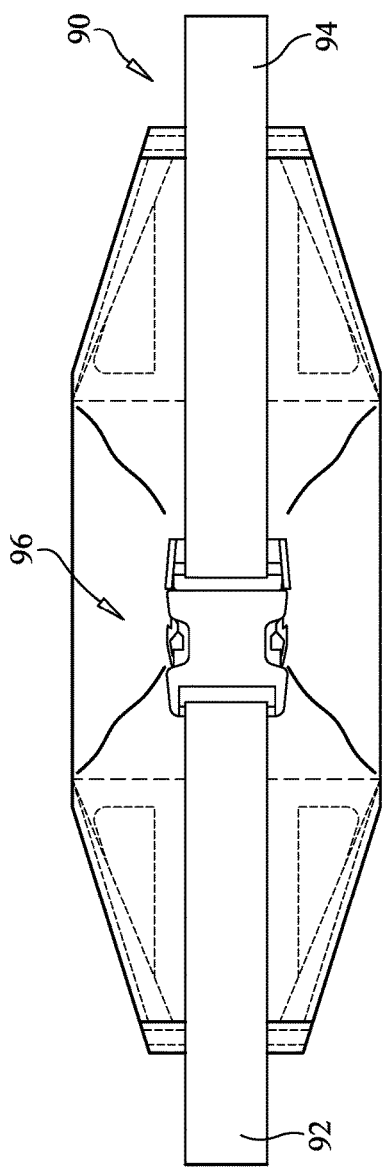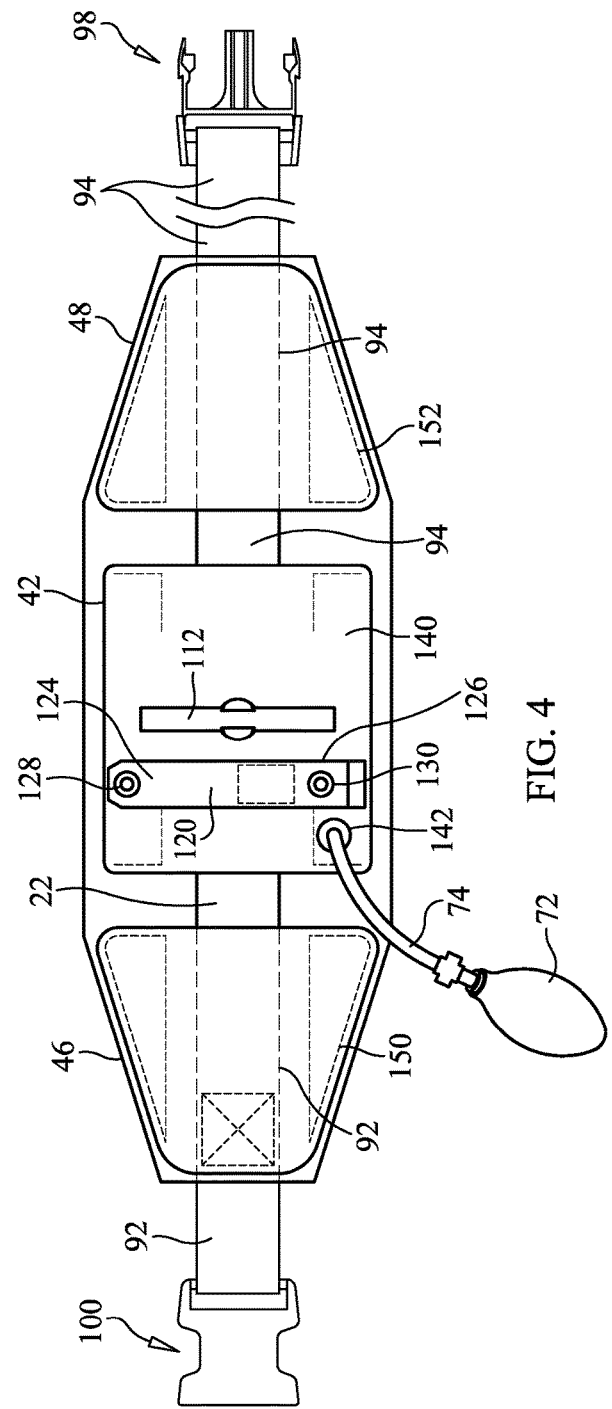

ABDOMINAL AORTIC TOURNIQUET

This application is a continuation of U.S. application Ser. No. 14/064,134, filed Oct. 26, 2013, now U.S. Pat. No. 9,351,737, issued May 31, 2016, which claims the benefit of and priority to U.S. Provisional Patent Application Ser. No. 61/719,194, filed Oct. 26, 2012. Both applications are incorporated by reference in their entireties for all purposes.

FIELD OF THE INVENTION

The present invention is directed to an abdominal aortic tourniquet which is an improvement over previous abdominal aortic tourniquets.

BACKGROUND OF THE INVENTION

A prior art design for an abdominal aortic tourniquet can be seen in published pending application Ser. No. 12/150,728 listed John Croushorn as inventor ("the '728 Application"), the '728 Application is incorporated by reference in its entirety particularly for its discussion on using an abdominal aortic tourniquet for occluding blood flow. The prior art design is intended to occlude the descending aorta at the bifurcation into the left and right iliac arteries. The prior art design is a non-invasive device intended for cross-clamp of the descending aorta. The primary use for the prior art design is for pelvic and lower extremity penetrating trauma is typically not treatable out in the field with a conventional tourniquet application. In use of the prior art design, the device is buckled around the patient, the bladder is positioned over the umbilicus, the provided belt is tightened by pulling a strap and then a windlass and the bladder is inflated to the appropriate pressure.

In detail the prior art has provided a portable pneumatic aortic occlusion device that is comprised of the following components:

(1) A torso securing strap made of webbing (with or without hook & loop fasteners attached to the webbing). The webbing is attached to the Compression Latch and goes around the torso just above the iliac crest;

(2) A base plate made of injected molded plastic which is used to connect the pressure application mechanism to the torso securing strap and to provide a stable platform for anchoring the directed bladder. The base plate contains an offset orifice which allows the pressure tubing to connect from the inflation mechanism to the bladder. A retention clip may be used to retain the tubing if a hand drive pressure pump is utilized. A separate retention clip may be incorporated to retain a CO2 cartridge on a CO2 cartridge variation. The underside of the base plate is lined with a foam padding that extends beyond the edges of the base plate;

(3) A directed bladder on the underside of the base plate is a self-contained pneumatic bladder. A valve stem is incorporated in the bladder.

(4) A threaded CO2 Cartridge for the CO2 variation or a hand driven pressure pump;

(5) A bladder sleeve to cover the bladder to protect it from exterior puncture or environmental exposure. The bladder sleeve may be physically attached to the bladder allowing it to be fully compressed when the bladder is empty of air;

(6) An optional pressure release valve to aid in securing the bladder pressure once inflated;

(7) A right angle elbow connector to connect the CO2 cartridge to the Presta Valve stem; and (8) A three-part compression having a two hinged latch to provide final compression on the abdomen with the compression webbing.

When constructing the prior art design the latch is prepared separately or purchased already assembled prior to assembly of the device. The torso securing strap is prepared by cutting a 120 cm piece of 4 cm nylon webbing. Hook and loop fasteners may or may not be attached to one side of the webbing. The torso securing strap is attached at one end to the compression latch (the terminal arm of the latch) by 4 rivets. The latch base is fixed to the base plate with one piece of looped webbing anchored between the latch and the base plate by 4 rivets. This loop of material is what the buckle is fixed to. The base plate foam pad is placed on the underside of the base plate (side toward patient). The bladder is positioned under the base plate. The valve stem is passed up through the orifice prepared in the base plate and secured by a small washer and the stem nut. A bladder sleeve is positioned over the top of the bladder and attached to the underside of the base plate. With the CO2 variation, the elbow connector and threaded CO2 cartridge are packaged with the pneumatic aortic compression system With manual inflator variation using a hand pump, the bulb pump to include the pressure valve and one way valve at the base of the pump is bought commercially or prepared separately. The tubing is permanently fixed to the bladder. A pressure gauge for warning if the pressure is dropping in the bladder or maximum pressure has been reached can be provided.

To use the prior art design the torso securing strap is fed around the patient's body with the strap lying above the iliac crests. It is fed through both slots in the buckle. The base plate is positioned just left of midline. The slack should be removed from the strap. The latch is closed. The Presta valve is opened and the elbow connector applied to the Presta valve stem. The CO2 threaded cartridge is attached to the elbow connector. The cartridge is screwed to its maximum depth to penetrate the cartridge. The cartridge is gently unscrewed to release air into the bladder. The flow of CO2 can be stopped by screwing the cartridge into the elbow connector. A pressure indicator may be incorporated on the device to warn if high pressure exists in the bladder or that the pressure is falling. Generally the bladder is inflated until he desired effect of cessation of bleeding occurs, or the desired effect of preload return to the heart is achieved. If a manual bulb hand-pump can be utilized in place of the CO2 cartridge.

This prior art design requires a separate gas holding inner bladder and outer shell cover, and despite its objectives is also known to not provide for sufficient point pressure required to occlude an artery. The present invention provides for an improved abdominal aortic tourniquet which overcomes the problems of the prior art two-piece design and insufficient amount of point pressure.

SUMMARY OF THE INVENTION

The present invention provides for a novel bladder shape for an abdominal aortic tourniquet that provides for a significant improvement of prior art designs. The bladder shape of the prior art design is similar to a pillow which does not provide for a correct point pressure required to occlude the artery. The substantially triangular or triangular cross-section shape of the present invention bladder, corrects this problem in the art, and provides for the appropriate amount of point pressure which results in the occluding of the artery.

Certain non-limiting novel aspects of the present invention are its improved design and construction yielding a one-piece design (i.e. as opposed to a separate bladder and separate bag/cover) having a novel shape when inflated that significantly increases the amount of point pressure such that the intended artery is properly occluded. The one-piece design of the present invention provides for a reduction in cost of materials and provides for a more compact piece as compared to prior designs.

Other non-limiting improvements of the present invention device over the prior designs include using a thumb wheel valve as opposed to the 3-way stopcock, using a preferred 200 denier weight material and the locations of the buckles.

Thus, the present invention provides for a single piece of weldable and gas impermeable fabric that is configured in a novel manner to create a three-dimensional, pneumatic piston while also serving as storage/transport cover, attachment structure, and major component of the belt member.

BRIEF DESCRIPTION OF THE INVENTION

FIG. 3 is a back side view of the abdominal aortic tourniquet of FIG. 1 showing the belt ends connected with a non-limiting side release buckle;

FIG. 4 is a front side view of the abdominal aortic tourniquet of FIG. 1;

DETAILED DESCRIPTION OF THE INVENTION

Figure 5:
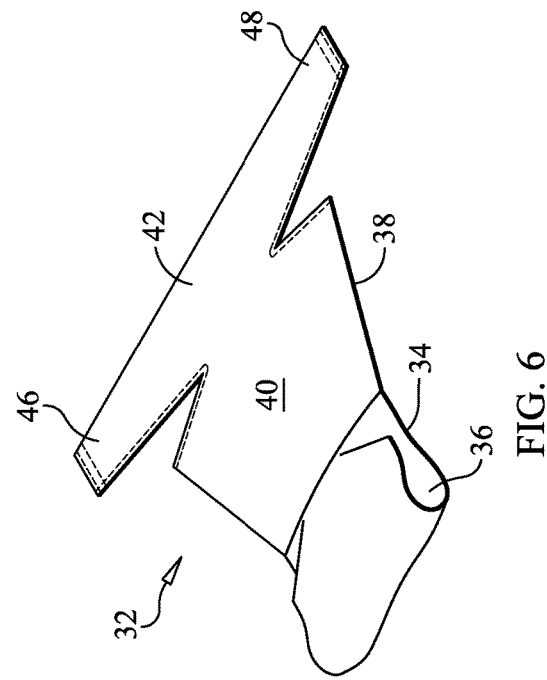
FIG. 5 is a perspective view of the one-piece bladder, pocket and wings member in accordance with the present invention shown in an open flat configuration.
Figure 6:
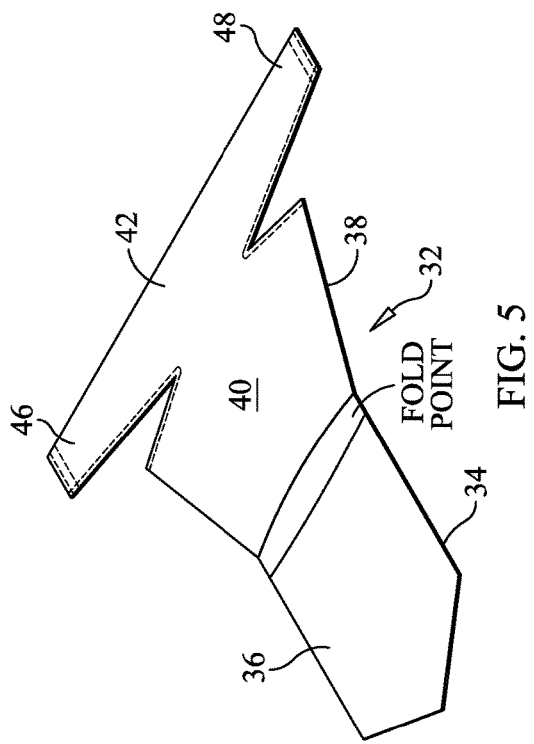
FIG. 6 is a perspective view of the one-piece member of FIG. 5 showing the bladder about to be inserted within the pocket.
Figure 7:
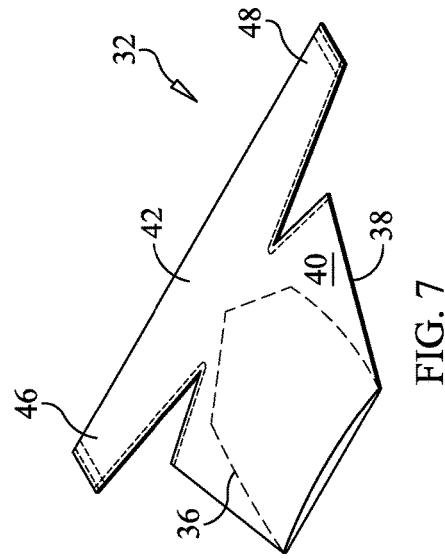
FIG. 7 is a perspective view of the one-piece member of FIG. 5 showing the bladder fully inserted and received by the pocket.
Figure 8:
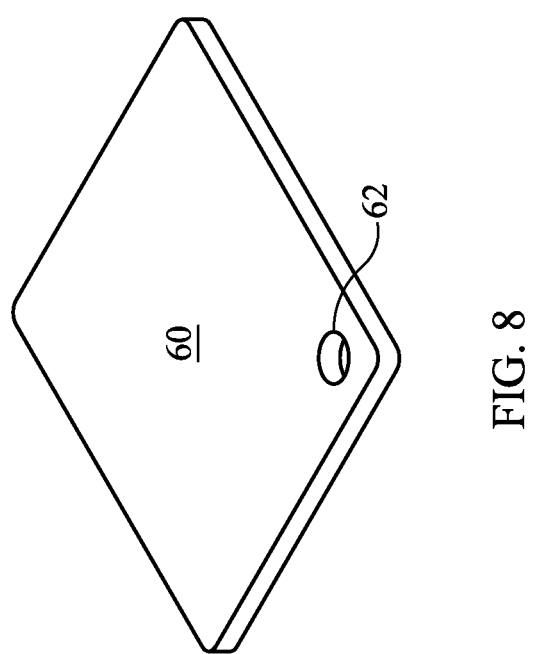
FIG. 8 is a perspective view of an internal plate for the abdominal aortic tourniquet of FIG. 1 in accordance with the present invention.

As seen in FIGS. 1 through 8, a first embodiment for an abdominal aortic tourniquet is shown with tourniquet generally designated as reference number 20. As best seen in FIGS. 5-7, tourniquet 20 can comprise a monolithically formed one-piece member 32 having a first sealed section 34 to form a bladder 36, a second section 38 forming a receiving pocket 40 and a top section 42. Bladder 36 is formed from welding portions of first sections 34 together though such is not considered limiting and other known methods for creating a sealed bladder can also be used and are considered within the scope of the invention. As seen in FIG. 5, when one-piece member 32 is in a flat or unfolded configuration, prior to assembly of tourniquet, second section 38 is positioned above first section 34 and top section 42 is above second section 38. As best seen in FIG. 6, one-piece member 32 is folded at a point between first section 34 and second section 38 such that first section 32, including sealed bladder 36 is inserted within the receiving pocket 40 (See FIG. 7). Thus, receiving pocket 40 acts as a cover for bladder 36, while allowing for both a cover and a bladder to be one-piece and not separate pieces or parts.

For the embodiments shown in FIGS. 1 and 9-11 of the present invention, one-piece member 32 can also be provided with a first wing 46 and a second wing 48 protruding outwards from respective sides of top section 42 (See FIG. 5). Wings 46 and 48 are preferably monolithically formed with the other portions of one-piece member 32. In use, wings 46 and 48 help to stabilize the one-piece member 32 when one-piece member is secured to the user as described below. Wings 46 and 48 help to prevent one-piece member from rotating when bladder 36 is inflated during use of tourniquet 20 to occlude a desired artery of the user or another location on the user for other medical purposes.

One-piece member 32 is a one-piece member is a single piece of weldable and gas impermeable fabric and can be preferably constructed from a nylon reinforced fabric polyurethane coated and radio frequency weldable or a polyurethane laminated nylon reinforced radio frequency weldable fabric, though such is not considered limiting and other materials which provide the desired characteristics and functions of the present invention can also be used and are considered within the scope of the invention.

A plate 60 (FIG. 8) can secured to an internal surface of the top section 42. In use, plate 60 aids in exerting force and pushing the inflated bladder 36 into the person for the intended blood flow occluding. Plate 60 can be constructed from ABS or other similar materials though such is not considered limiting and other materials that will plate 60 to function properly can also be used and are considered within the scope of the invention. Plate 60 is preferably secured to top section 42 by stitching, though such is not considered limiting and other securement techniques can be used and are considered within the scope of the invention. Plate 60 can be provided with an opening or aperture 62 to permit an airline 74 of a manual inflator 70 to pass through. Aperture 62 can be circular or substantially circular in shape though such is not considered limiting and other shapes for aperture 62 can be chosen. A corresponding aperture 44 (See FIG. 9) can be provided in top section 42 for similar purposes as plate aperture 62. Top section aperture 44 can be similar in shape to plate aperture 62 or can be of a different shape. When plate 60 is secured to an internal surface (internal when assembled) of top section 42 plate aperture 62 can be aligned or substantially aligned with the top section aperture 44.

An inflation member is in communication with bladder 36 in order to inflate bladder 36. In a preferred embodiment, the inflation member can be a manual inflator 70 comprising a hand pump or bulb 72 and gas or air line, hose, tube, etc. (collectively referred to as airline 74) connected at one end to hand pump 72 and at a second end to bladder 36 by conventional means such as, but not limited to, valve/elbow mechanism. Hand pump 72 is used conventionally, such that squeezing hand pump 72 repeatedly will result in bladder 36 being inflated. Other conventional automatic and manual inflator mechanisms, such as CO2 cartridges, etc. can also be used to inflate bladder 36 and are also considered within the scope of the invention.

A belt, webbing, strap, etc. (collectively referred to as "belt 90") can be secured to one-piece member 32, such as, by stitching 92 at top section 42. Belt 90 is used for maintaining one-piece member 32 on a user after one piece member 32 has been positioned at the desired point on the user and continues to maintain the position of one-piece member 32 with respect to the user also after bladder 36 is properly inflated by the inflation member. Belt 90 can include a first belt portion 92 and a second belt portion 94. A conventional belt attachment mechanism can be provided for securing first belt portion 92 to second belt portion 94. In one non limiting embodiment, the attachment mechanism can be a side release buckle 96. Other buckle types, snaps, button/buttonholes, hook and loop fasteners, etc. can also be used to connect first belt portion 92 to second belt portion 94 and are also considered within the scope of the invention. Side release buckle includes a male portion 98 preferably associated with second belt portion 94 and a mating female portion 100 preferably associated with first belt portion 92. It is also within the scope of the invention to associate female portion 100 with second belt portion 94 and associate male portion 98 with first belt portion 92. Preferably, the length of belt 90 is adjustable and by preferably providing a belt length adjustable member with female portion 100. Alternatively, the belt length adjustable member can be provided with male portion 98 or both male portion 98 and female portion 100 can be provided with belt length adjustable members. All configurations are considered within the scope of the invention. Where the adjustable member is provided with female portion 100 only, once one-piece member 32 is positioned at its desired location on the user, the belt portions 92 and 94 are connected to each other by mating male portion 98 with female portion 100, second belt portion is pulled to tighten the securement of one-piece member 32 to the user.

To increase the tightness of the securement of one-piece member 32 to the user, a tightening mechanism can be provided. In one non-limiting embodiment, a windlass mechanism 110 is provided for such purposes. Windlass mechanism can include a handle 112, a handle strap 114 secured to handle 112, a first belt connecting strap 116 secured at one end to an end of first belt portion 92 and at a second end to handle strap 114, and a second belt connecting strap 118 secured at one end to an end of second belt portion 94 and at a second end to handle strap 116.

Figure 1:
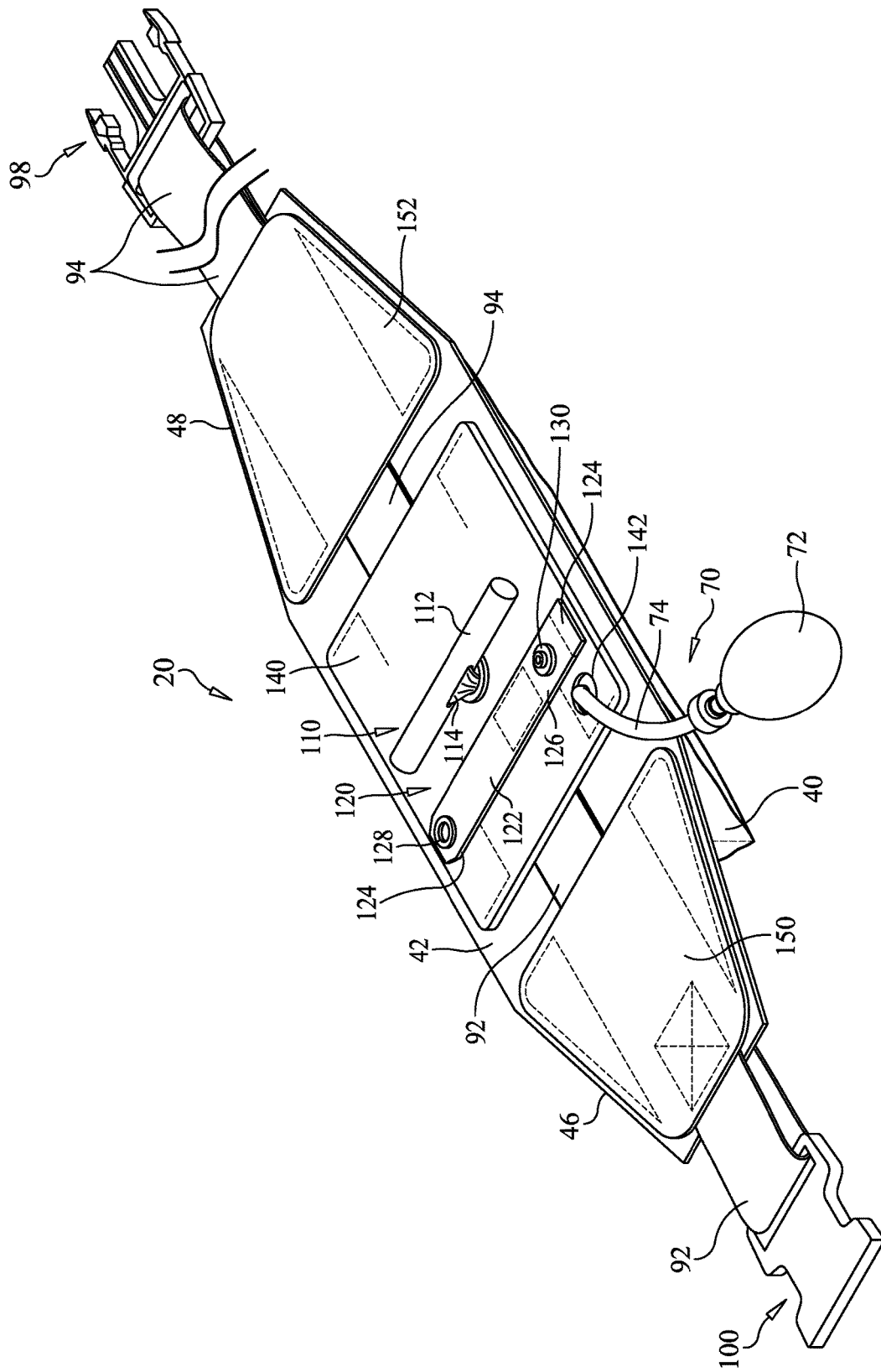
FIG. 1 is a top perspective view of a first embodiment for an abdominal aortic tourniquet in accordance with the present invention.

The embodiment shown in FIG. 1 can include an external plate 140, which can be constructed from a carbon fiber, ABS or other conventional materials, secured to an external surface of top section 42, such as by stitching or other conventional attachment methods. Plate 140 can be provided with an aperture 142 which is aligned or substantially aligned with apertures 44 and apertures 62 to permit airline 72 to pass through. Plate 140 also help or aids in maintaining the proper position of first belt portion 92 and second belt portion 94 along top section 42 of one-piece member 32. Similarly for further position maintenance of belt portions 92 and 94, external side plates 150 and 152 can be secured to wing members 46 and 48, respectively, by conventional means such as, but not limited to, stitching, etc. Belt passageways are defined between wings members 46 and 48 and plates 150 and 152 for feeding belt portions 92 and 94 therethrough, respectively. Belt portions are maintained in position within the belt passageways but are movable for purposes of tightening. Side plates 150 and 152 can be constructed from the same material as external plate or from other conventional materials.

Windlass mechanism 110 can also include a handle holder 120 consisting of a strap 122 having a first portion 124, a second portion 126, a first female snap member 128 attached to first portion 124 and a mating second male snap member 130 attached to second portion 126. Other mechanism, such as, but not limited to, button/buttonholes, hook and loop fasteners, etc. can also be used in lieu of snap member 128 and 130 and are also considered within the scope of the invention. Additionally, male snap member 130 can be provided with first portion 124 and second snap member 128 can be provided with second portion 126 and such configuration is also within the scope of the invention. In the embodiment shown in FIG. 1, handle holder is secured to external plate, by permanently attaching second portion 126 to external plate, by stitching, sewing or other conventional means. First portion 124 is movable and can be folded to allow female portion 128 to mate with male portion 130 to form a handle insertion loop.

Figure 9:
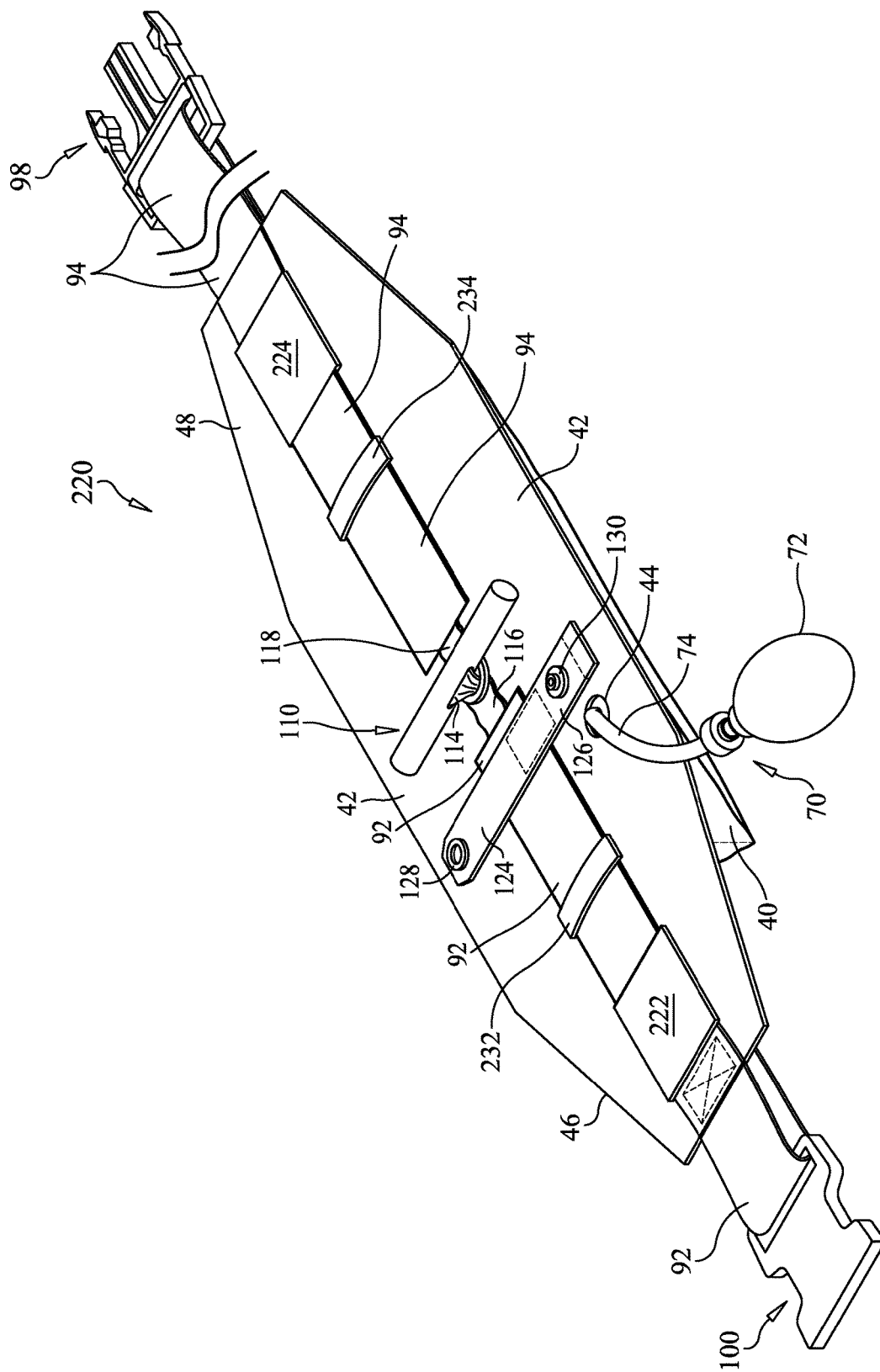
FIG. 9 is a top perspective view of a first alternative embodiment for the abdominal aortic tourniquet in accordance with the present invention.
Figure 11:
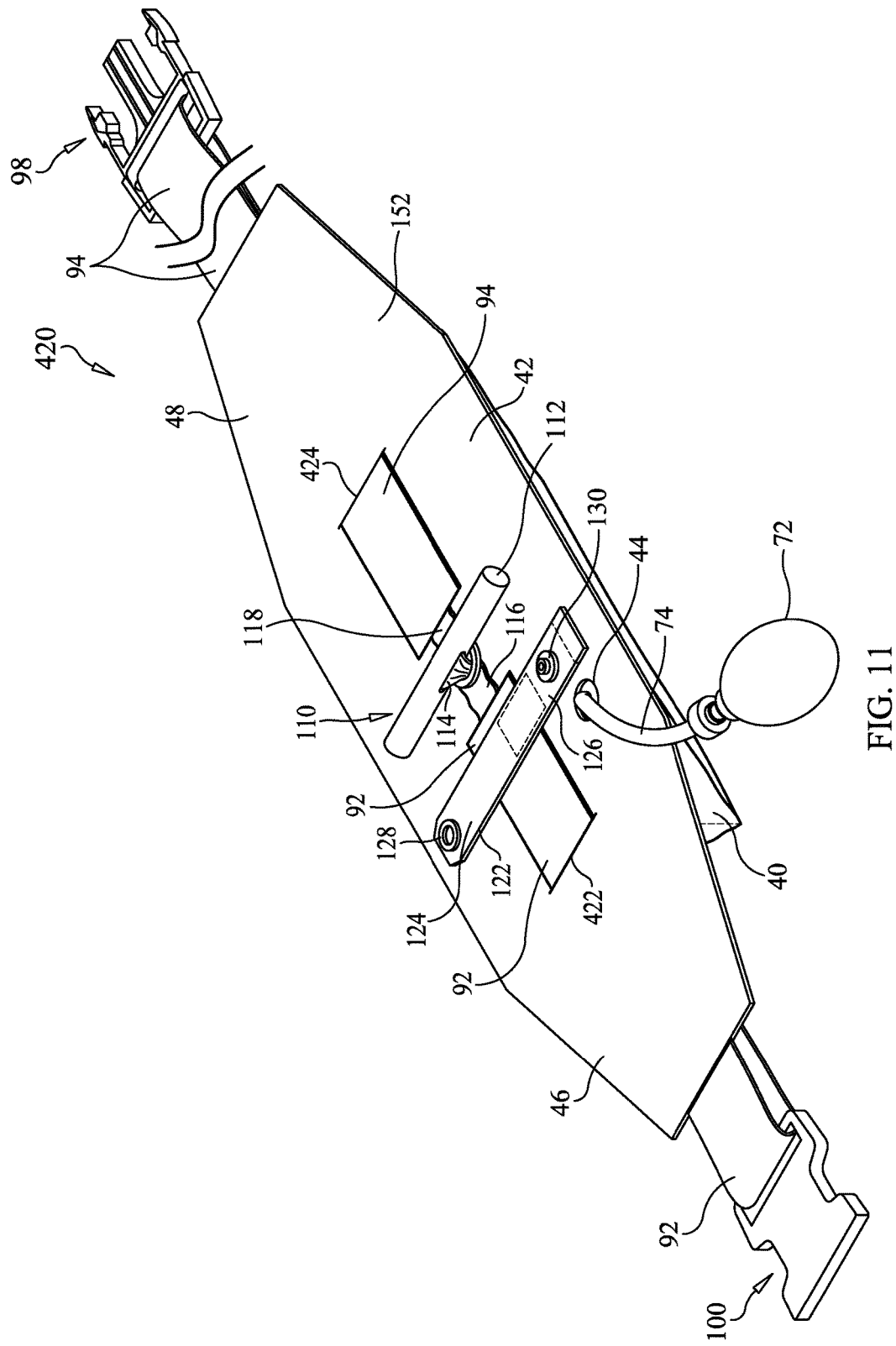
FIG. 11 is a top perspective view of a third alternative embodiment for the abdominal aortic tourniquet in accordance with the present invention.

The side of first portion 124 not associated with female portion 128 can be provided with a non-permanent attachment member, such as, but not limited to, a first portion of a hook and loop fastener and a second mating hook and loop fastener can be secured to external plate 140 by conventional means, such as glues, adhesives, tapes, etc. Thus, prior to needing to use handle holder 120 first portion 124 can be held in place and not hanging by the mating of the hook and loop fasteners.

Where external plate 140 is not provided, such as, but not limited to, in the embodiments shown in FIGS. 9 and 11, windlass mechanism 110 can be associated directly with top section 42.

In use, with one-piece member 32 secured to the user by belt 90 and second belt portion 94 pulled to tighten the securement, windlass handle 112 is then turned/twisted which causes belt connection straps 116 and 118 to pull respective belt portions 92 and 94 inward to further tighten the connection of one-piece member 32 to the user. In order to maintain belt portions 92 and 94 in their inward position, one end of windlass handle 112 is inserted within the loop creating by mating snap portions 128 and 130 to maintain the handle in its current twisted position.

Figure 2:
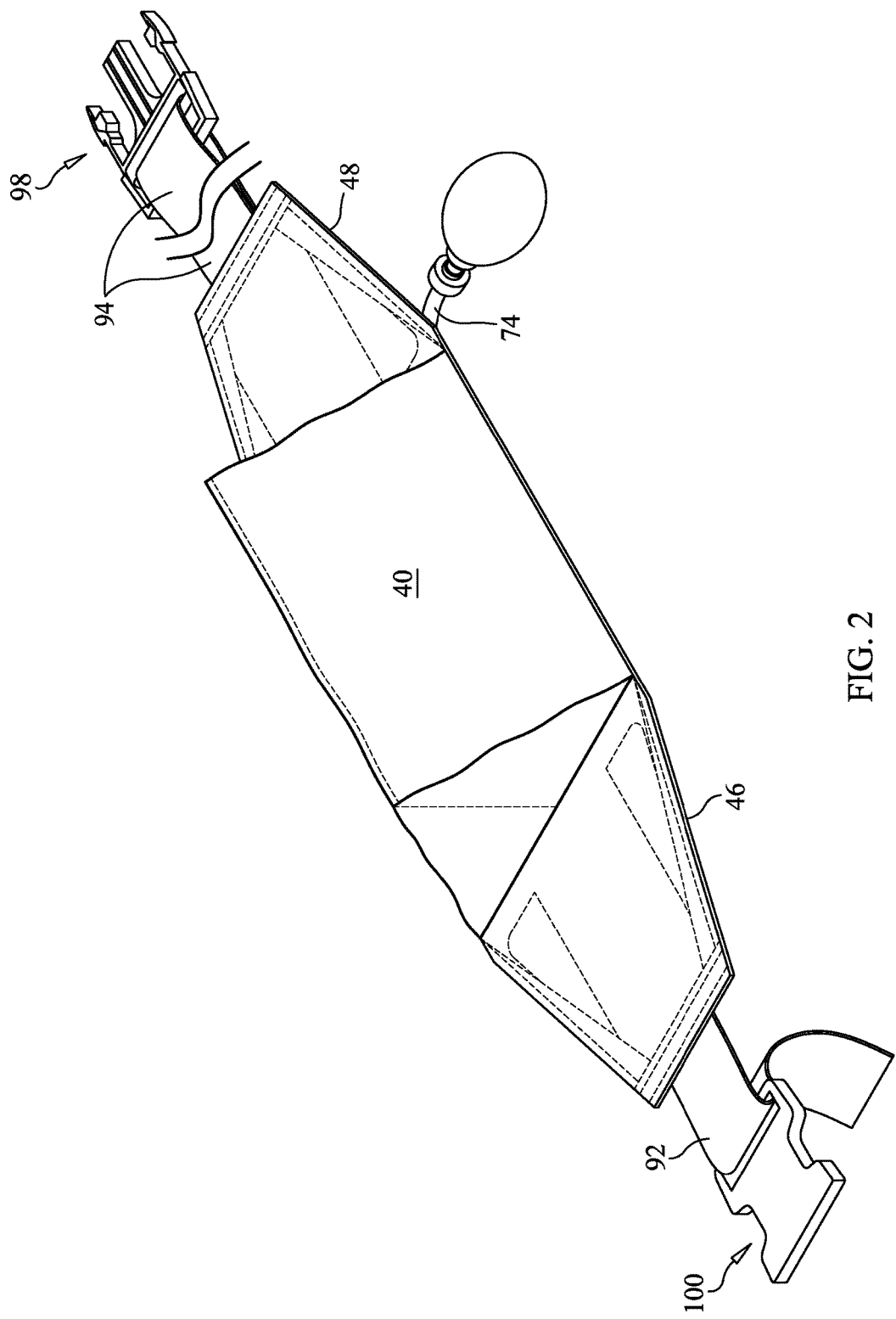
FIG. 2 is a bottom perspective view of the abdominal aortic tourniquet of FIG. 1.

At this point, bladder 36 is ready for inflating by the inflation member. As best seen in FIG. 2, bladder 36 has a substantially triangular cross-sectional shape when properly inflated by the inflation member to emphasize a pressure point for occluding the desired artery, blood vessel, etc. (i.e. abdominal aortic artery, etc.). As seen in FIG. 5, in a flat configuration prior to assembly, first section 32 can be substantially shaped as an upper square or rectangle portion 33 having a sealed top edge 35 and a lower triangle portion 37. Upper square or rectangle portion 33 and lower triangle portion 37 are in communication with each other and together, where welded, defined bladder 36. Second section 38 is provided with an open bottom end 39 which forms the opening of receiving pocket 40. A first side 41 of second section 38 can taper outward from a one side of bottom end 39 and a second side 43 of second section can taper outward from a second side of bottom end 39. A top end 45 of second section 38 can also be open.

Once tourniquet 20 is assembled, originally open bottom end 39 can be closed or sealed by conventional means such as sewing or welding (though not considered limiting) to help retain bladder 36 within receiving pocket 40. Alternatively, bottom end 39 can remain open and bladder 36 can remain within pocket 40 by its position with respect to the user and/or its inflation causing it to expand within pocket 40. In view of how bladder is welded, when bladder 36 is inflated by the inflation member lower triangle portion 37 flattens out and contacts internally located plate 60 and sealed top edge 35 of upper square or rectangle portion 33 becomes the tip or point 31 of a substantially triangular or triangular cross-sectional shaped bladder 36 and with bladder 36 enclosed within second section 38 of one-piece member 32. The point where wing members 46 and 48 and second section 38 meet can also be kept open at the top of second section 38 or can be closed by conventional means. Bladder 36 can be provided with any overpressure and/or relief valve, if desired.

The various folds/welding/sewing for one-piece member 32 and the steps for constructing the present invention tourniquet are detailed in our Provisional Patent Application Ser. No. Ser. No. 61/719,194, filed Oct. 26, 2012, which is incorporated by reference in its entirety. The shape of present invention bladder 36 addresses problems with prior designs, and provides for the appropriate amount of point pressure which results in the occluding of the artery.

Certain non-limiting novel aspects of the tourniquet 20, as well as the alternative embodiments discussed below, include, but are not limited to, its improved design and construction yielding a one-piece design (i.e. as opposed to a separate bladder and separate bag/cover of prior designs) having a novel bladder shape when inflated that significantly increases the amount of point pressure such that the intended artery is occluded.

The novel construction method (incorporating welding and sewing techniques) used to construct the tourniquets described herein reduces the cost of materials and provides for a more compact piece. Other non-limiting improvements found in the described tourniquets of the present invention over prior designs include using a thumb wheel valve as opposed to the 3-way stopcock, using a preferred 200 denier weight material and the locations of the buckles.

Thus, the tourniquets of the present invention provides for a single piece of weldable and gas impermeable fabric 32 that is configured in a novel manner to create a three-dimensional, pneumatic piston while also serving as storage/transport cover, attachment structure, and major component of the belt member. By providing a single-piece member 32, the present invention reduces material, labor, storage and shipping costs as compared to the prior art design.

FIG. 9 illustrates a second embodiment for an abdominal aortic tourniquet of the present invention and is generally illustrated as reference numeral 220. In this embodiment, plates 60, 150 and 152 have been eliminated and fabric sleeves 222 and 224 are secured to wings 46 and 48, respectively, to serve as the belt portion position maintainers. Sleeves 222 and 224 are preferably sewn to wings 46 and 48. However, any conventional methods for securing can be used and are considered within the scope of the invention. Similar fabric loops 232 and 234 are provided for maintaining the position of belt portions 92 and 94 that were maintained by plate 60 in the embodiment shown in FIG. 1. Fabric loops 232 and 234 can also be preferably sewn to top section 42, though other conventional securement methods can also be used and are considered within the scope of the invention. The operation of tourniquet 220 and the remaining parts of tourniquet 220 are similar to those described above for the tourniquet embodiment of FIG. 1.

Figure 10:
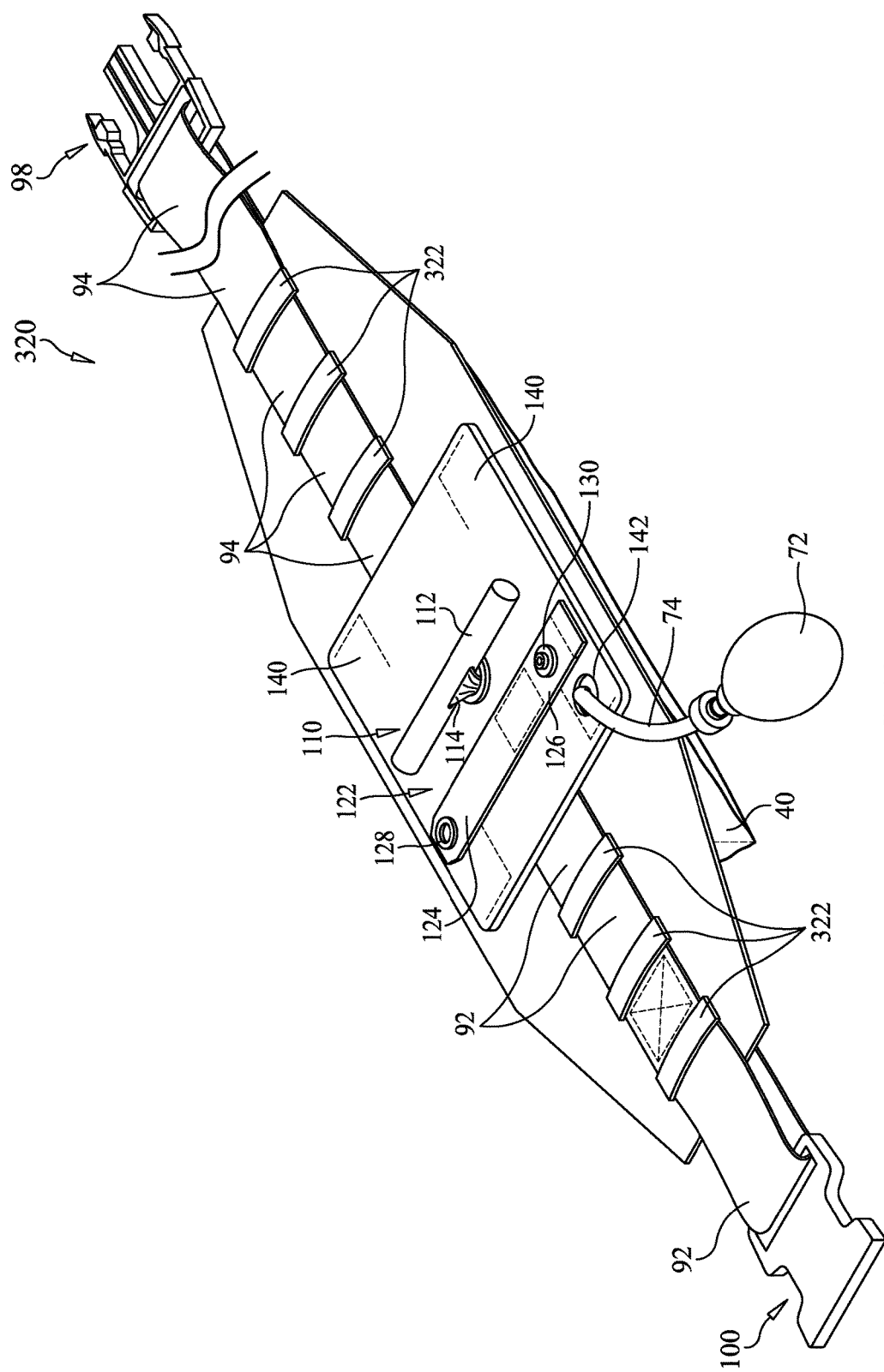
FIG. 10 is a top perspective view of a second alternative embodiment for the abdominal aortic tourniquet in accordance with the present invention.

FIG. 10 illustrates a third embodiment for an abdominal aortic tourniquet of the present invention and is generally illustrated as reference numeral 320. In this embodiment, plates 150 and 152 have been eliminated and one or more fabric loops 322 are secured to wings 46 and 48 to serve as the belt portion position maintainers. Loops 322 are preferably sewn to wings 46 and 48. However, any conventional methods for securing can be used and are considered within the scope of the invention. The operation of tourniquet 320 and the remaining parts of tourniquet 320 are similar to those described above for the tourniquet embodiment of FIG. 1.

FIG. 11 illustrates a fourth embodiment for an abdominal aortic tourniquet of the present invention and is generally illustrated as reference numeral 420. In this embodiment, plates 60, 150 and 152 have been eliminated. In this embodiment, the thickness of wings 46 and 48 at least at their outer ends is increase such that a belt receiving slot can be provide at the outer ends of wings 46 and 48. Additionally, belt receiving slot 422 and 424 are also provided in top section 42. Belt portion 92 is maintained in position by being threaded through top section slot 422 and then through end slot of wing 46 and belt portion 94 is maintained in position by being threaded through top section slot 424 and then through end slot of wing 48. The operation of tourniquet 220 and the remaining parts of tourniquet 220 are similar to those described above for the embodiment of FIG. 1.

Figure 12:
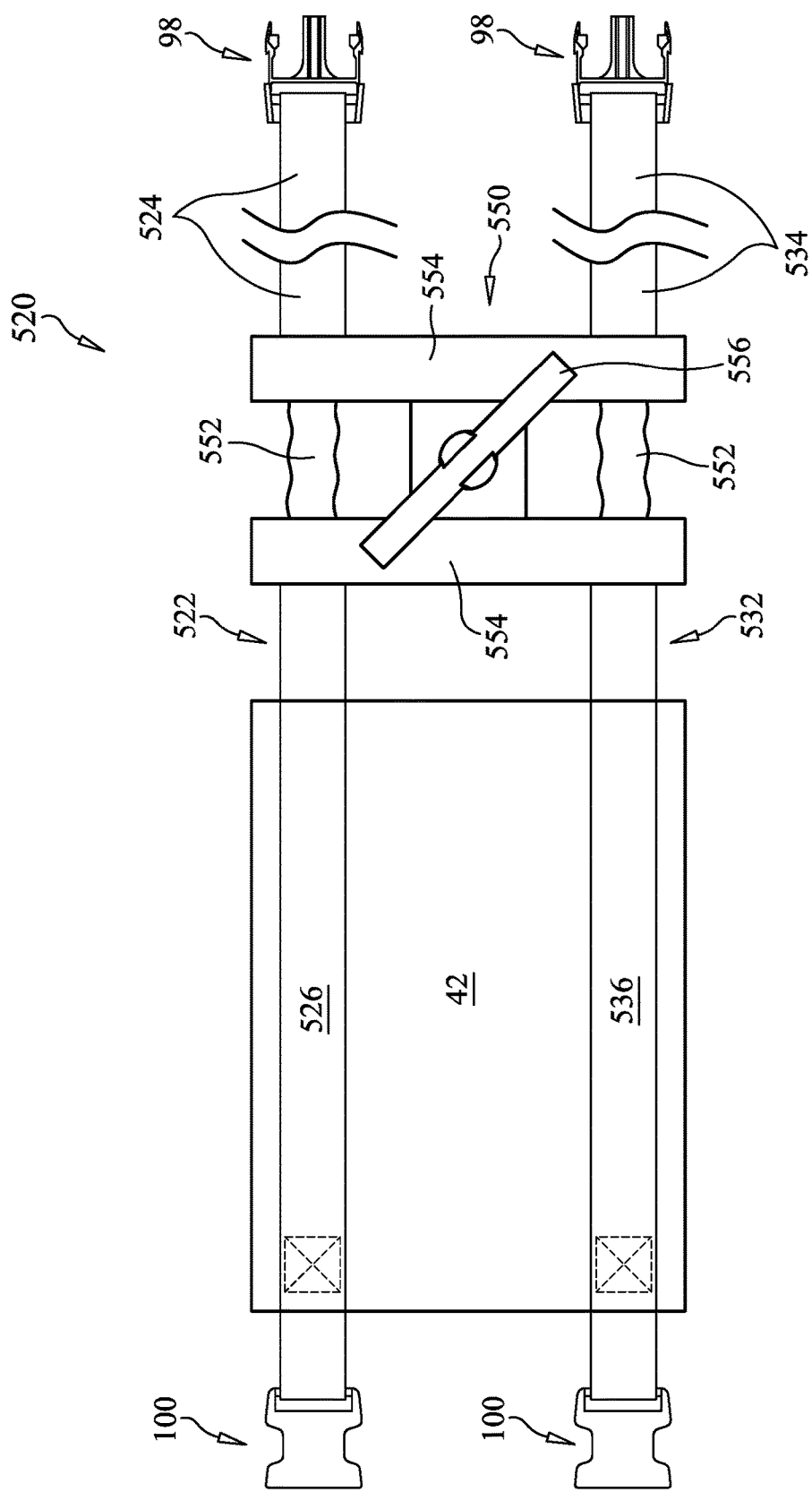
FIG. 12 is a top view of a fourth alternative embodiment for the abdominal aortic tourniquet in accordance with the present invention.

FIG. 12 illustrates a fifth embodiment for an abdominal aortic tourniquet of the present invention and is generally illustrated as reference numeral 520. In this embodiment, plates 60, 150 and 152 have been eliminated, as well wings 46 and 48. In this embodiment, two belts 522 and 532 are provided, with belt 522 at a one end of top section 42 of one-piece member 32 and belt 532 at an opposite end of top section 42. The location of the two belts provides for the stabilization of one-piece member 32 when bladder 36 is inflated and therefore wings 46 and 48 can be removed (though it is also within the scope of the invention to include wings for this embodiment as well). Belt 522 can include a first belt portion 524 and a second belt portion 526. A portion of second belt portion 526 can be secured to top section 42 by conventional means, such as, but not limited to, stitching. Belt 532 can include a first belt portion 534 and a second belt portion 536. A portion of second belt portion 536 can be secured to top section by conventional means, such as, but not limited to, stitching. Belt portions 524 and 526 and belt portions 534 and 536 will both be provided with similar belt connectors (i.e. side release buckle, etc.) as described above for the tourniquet embodiment shown in FIG. 1. A single windlass mechanism 550 can be provided for tightening both belts 522 and 532 at the same time, through the use of additional connecting straps 552 and cross straps 554. Windlass 550 operates similar to the windlass mechanism described for the tourniquet embodiment shown in FIG. 1. A windlass handle holder, similar to strap 122, can be secured to one or both of the cross straps 554 for holding windlass handle 556 in its twisted position during use. The operation of tourniquet 520 and the remaining parts of tourniquet 520 are similar to those described above for the embodiment of FIG. 1.

It is also within the scope of the invention to configure further embodiments for maintaining the belt portion positions using various combinations of external plates, fabric sleeves, fabric loops, wing constructions and/or slots and all configurations are also within the scope of the invention.

Additional features that can be used with the present invention include providing a protective armor covering through use of body armor material stitched or otherwise secured directly or indirectly to the bladder. Another non-limiting feature can comprise, an initially separate outer sleeve of body armor material that is then finally RF welded in an outer layer of "BC" material and has a vacuum port that allows the device to be highly compressed by pulling a vacuum at final assembly and/or inspection, then sealing off. This non-limiting feature can be achieved by a check valve that can slide into an elbow tube like member in the RES, only installed in reverse. With this feature the present invention device can be submerged in water and still remain armored (body armor is rendered non-compliant once wetted), and while also protecting the vital pump and pneumatic parts from water/debris intrusion. The outer layer of BC material can be sealed closed on a small bar welder after the entire device is signed off and inserted into a "waterproof to 300-meters" ballistic protective sleeve. A "cut here line" or similar language can be provided on the sleeve to instruct the user where to open.

When positioned at a different location on the user, the tourniquet embodiments of the present can also be used as part of a Micro-CPR simulator device. Thus, the various above-described present invention tourniquets used for occluding abdominal aortic arteries can be converted into a manual or automatic CPR device by attaching an electromechanical pump with inflate-deflate valve/timing system or a pneumatic pump from local air source or portable compressed gas cylinder or pneumatic foot pump. Other pumping sources can also be used and are considered within the scope of the invention. Also, as an alternative to electric timing device controls inflate/deflate valve control sequencing can be to place a large bore OPV in-line with the pump that has a preset minimum time to reset after opening. This delay in reset of the valve can be designed to allow for sufficient deflation of the tourniquet prior to the subsequent re-inflation (next compression). A foot pump or hand pump similar to those used for inflatable boats can be used for this purpose.

All measurements, amounts, sizes, shapes, percentages, configurations, securement or attachment mechanisms, stitch or weld locations, dimensions, sealing members, numbers, ranges, part locations, values, percentages, materials, orientations, methods of manufacture, tightening mechanisms, etc. discussed above or shown in the drawing figures are merely by way of example and are not considered limiting and other measurements, amounts, sizes, shapes, percentages, configurations, securement or attachment mechanisms, stitch or weld locations, dimensions, sealing members, numbers, ranges, part locations, values, percentages, materials, orientations, methods of manufacture, tightening mechanisms, etc. can be chosen and used and all are considered within the scope of the invention.

Furthermore, one or more features, components, parts or characteristics discussed for one embodiment of the present invention can also be used with another of the above discussed embodiments of the present invention.

Dimensions of certain parts as shown in the drawings may have been modified and/or exaggerated for the purpose of clarity of illustration and are not considered limiting.

Unless feature(s), part(s), component(s), characteristic(s) or function(s) described in the specification or shown in the drawings for a claim element, claim step or claim term specifically appear in the claim with the claim element, claim step or claim term, then the inventor does not considered such feature(s), part(s), component(s), characteristic(s) or function(s) to be included for the claim element, claim step or claim term in the claim for examination purposes and when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. An abdominal aortic tourniquet, comprising:
   a member having a first sealed section to form a bladder and a second section defining a receiving pocket and a top section, said member folded between said first sealed section and said second section such that said first sealed section is inserted within the receiving pocket;
   an inflation member in communication with said bladder; and
   a belt secured to said member adapted for maintaining the one piece member on a user when said bladder is inflated by said inflation member.

2. The abdominal aortic tourniquet of claim 1 wherein said bladder has a substantially triangular cross-sectional shape when inflated.

3. The abdominal aortic tourniquet of claim 1 wherein said member further includes a first wing section extending from a first side of said top section and a second wing section extending from a second side of said top section.

4. The abdominal aortic tourniquet of claim 1 further comprising a windlass mechanism in communication with said belt, said windlass mechanism adapted for tightening the belt with respect to the user prior to inflating said bladder with said inflation member.

5. The abdominal aortic tourniquet of claim 1 wherein said inflation member is a manual air pump having a hand squeezable bulb and airline, said airline having a first end attached to said hand squeezable bulb and a second end in communication with said bladder.

6. The abdominal aortic tourniquet of claim 5 further comprising a first plate secured to an internal surface of said top section; wherein said top section has an opening and said first plate has an opening, said top section opening aligned with said first plate opening when said first plate is secured to said top section, wherein said airline is inserted through said top section opening and said first plate opening.

7. The abdominal aortic tourniquet of claim 1 wherein said member is a single piece of weldable and gas impermeable fabric.

8. The abdominal aortic tourniquet of claim 1 wherein in a flat configuration prior to assembly said first section substantially shaped as an upper square or rectangle portion having a sealed top edge and a lower triangle portion, said upper square or rectangle portion and said lower triangle portion in communication with each other.

9. The abdominal aortic tourniquet of claim 8 wherein in a flat configuration prior to assembly said second section shaped to have an open bottom end, a first side tapering outward from a first side of said bottom end, a second side tapering outward from a second side of said bottom end and an open top end.

10. The abdominal aortic tourniquet of claim 9 wherein in an assembled configuration said first section is received within said second section and said second section is closed to enclose said first section.

11. The abdominal aortic tourniquet of claim 10 wherein said bladder is welded such that when in an assembled configuration and when said bladder is inflated said lower triangle portion flattens out; and said bladder forms the shape of a substantially triangular cross-sectional shaped prism and said sealed top edge of said upper square or rectangle portion becomes the tip or point of said substantially triangular cross-sectional shape prism.

12. The abdominal aortic tourniquet of claim 1 further comprising a first plate secured to an internal surface of said top section.

13. An abdominal aortic tourniquet, comprising:
   a member having a first sealed section to form a bladder and a second section defining a receiving pocket and a top section, said member folded between said first sealed section and said second section such that said first sealed section is inserted within the receiving pocket;
   a first plate secured to an internal surface of said top section;
   an inflation member in communication with said bladder; and
   a belt secured to said member adapted for maintaining the member on a user when said bladder is inflated by said inflation member; and
   a windlass mechanism in communication with said belt, said windlass mechanism adapted for tightening the belt with respect to the user prior to inflating said bladder with said inflation member;
   wherein said bladder has a substantially triangular cross-sectional shape when properly inflated by said inflation member.

14. The abdominal aortic tourniquet of claim 13 wherein said member further includes a first wing section extending from a first side of said top section and a second wing section extending from a second side of said top section.

15. The abdominal aortic tourniquet of claim 13 wherein said inflation member is a manual air pump comprising a hand squeezable bulb and airline, said airline includes a first end attached to said hand squeezable bulb and a second end in communication with said bladder; wherein said top section includes an opening and said first plate includes an opening, said top section opening aligned with said first plate opening when said first plate is secured to said top section, wherein said airline is inserted through said top section opening and said first plate opening.

16. The abdominal aortic tourniquet of claim 13 wherein said member is a single piece of weldable and gas impermeable fabric.

17. The abdominal aortic tourniquet of claim 13 wherein in a flat configuration prior to assembly said first section is substantially shaped as an upper square or rectangle portion having a sealed top edge and a lower triangle portion, said upper square or rectangle portion and said lower triangle portion in communication with each other; wherein in a flat configuration prior to assembly said second section is shaped to have an open bottom end, a first side tapering outward from a first side of said bottom end, a second side tapering outward from a second side of said bottom end and an open top end.

18. The abdominal aortic tourniquet of claim 17 wherein in an assembled configuration said first section is received within said second section and said second section is closed to enclose said first section.

19. The abdominal aortic tourniquet of claim 18 wherein said bladder is welded such that when in an assembled configuration and when said bladder is inflated said lower triangle portion flattens out and contacts said plate, said bladder forms the shape of a substantially triangular cross-sectional shaped prism and said sealed top edge of said upper square or rectangle portion becomes the tip or point of said substantially triangular cross-sectional shape prism.

20. A method for positioning a tourniquet on a user, said method comprising the steps of:
   (a) positioning a member against a desired point on a person's body, said member having a first sealed section to form a bladder, a second section defining a receiving pocket and a top section, said member folded between said bladder and said receiving pocket such that said bladder is disposed within said receiving pocket;
   (b) securing a first end of a belt to a second end of the belt to maintain the member in position with respect to the person, said belt secured to the member; and
   (c) inflating the bladder with an inflation member to a substantially triangle cross-sectional shape, wherein a plate member secured internally to the member contacts the bladder and helps to push pointed end of the inflated bladder into the person's body at the desired point.

21. The method for positioning a tourniquet on a user of claim 20 further comprising the step of tightening the belt with a windlass mechanism to tighten the securement of the member to the person's body.

* * * * *